(12) United States Patent
Altman et al.

(10) Patent No.: US 9,381,020 B2
(45) Date of Patent: Jul. 5, 2016

(54) PYLORIC OBSTRUCTION DEVICE

(71) Applicants: Nir Altman, Kfar Etzion (IL); Izhak Fabian, Kfar Truman (IL)

(72) Inventors: Nir Altman, Kfar Etzion (IL); Izhak Fabian, Kfar Truman (IL)

(73) Assignee: Easy Notes Ltd., Kfar Truman (IL)

( * ) Notice: Subject to any disclaimer, the term of this patent is extended or adjusted under 35 U.S.C. 154(b) by 0 days.

(21) Appl. No.: 14/467,013

(22) Filed: Aug. 24, 2014

(65) Prior Publication Data

US 2016/0051262 A1    Feb. 25, 2016

(51) Int. Cl.
*A61B 17/12* (2006.01)
*A61F 5/00* (2006.01)
*A61B 17/00* (2006.01)

(52) U.S. Cl.
CPC ..... *A61B 17/12172* (2013.01); *A61B 17/12031* (2013.01); *A61B 17/12036* (2013.01); *A61F 5/0079* (2013.01); *A61B 2017/00592* (2013.01); *A61B 2017/00615* (2013.01); *A61B 2017/00818* (2013.01); *A61B 2017/1205* (2013.01)

(58) Field of Classification Search
CPC ... A61F 2/04; A61F 2002/045; A61F 5/0076; A61F 5/0079
See application file for complete search history.

(56) References Cited

U.S. PATENT DOCUMENTS

| | | | | |
|---|---|---|---|---|
| 4,315,509 | A * | 2/1982 | Smit | 606/108 |
| 8,685,055 | B2 * | 4/2014 | VanTassel | A61B 17/12122 606/200 |
| 2005/0080444 | A1 * | 4/2005 | Kraemer et al. | 606/192 |
| 2007/0250150 | A1 * | 10/2007 | Pal | A61F 2/95 604/538 |
| 2008/0109087 | A1 * | 5/2008 | Durgin | 623/23.65 |
| 2012/0095483 | A1 * | 4/2012 | Babkes et al. | 606/153 |

* cited by examiner

*Primary Examiner* — Thomas J Sweet
*Assistant Examiner* — Daniel Bissing
(74) *Attorney, Agent, or Firm* — Dekel Patent Ltd.; David Klein

(57) ABSTRACT

An obstruction device includes an obstruction disc mounted on a shaft. The disc includes a membrane attached to a peripheral frame. An anchoring member extends from a distal portion of the shaft. The shaft, anchoring member and peripheral frame together have a unitary construction made from a bent slender element.

8 Claims, 3 Drawing Sheets

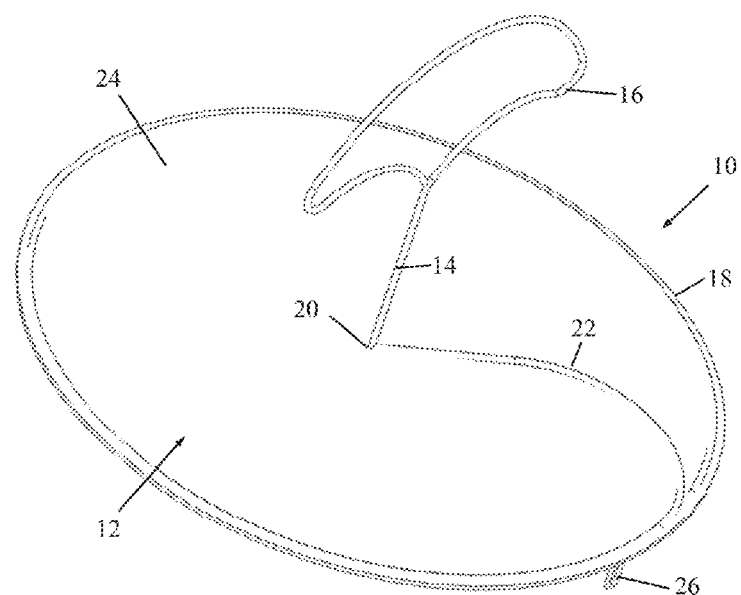
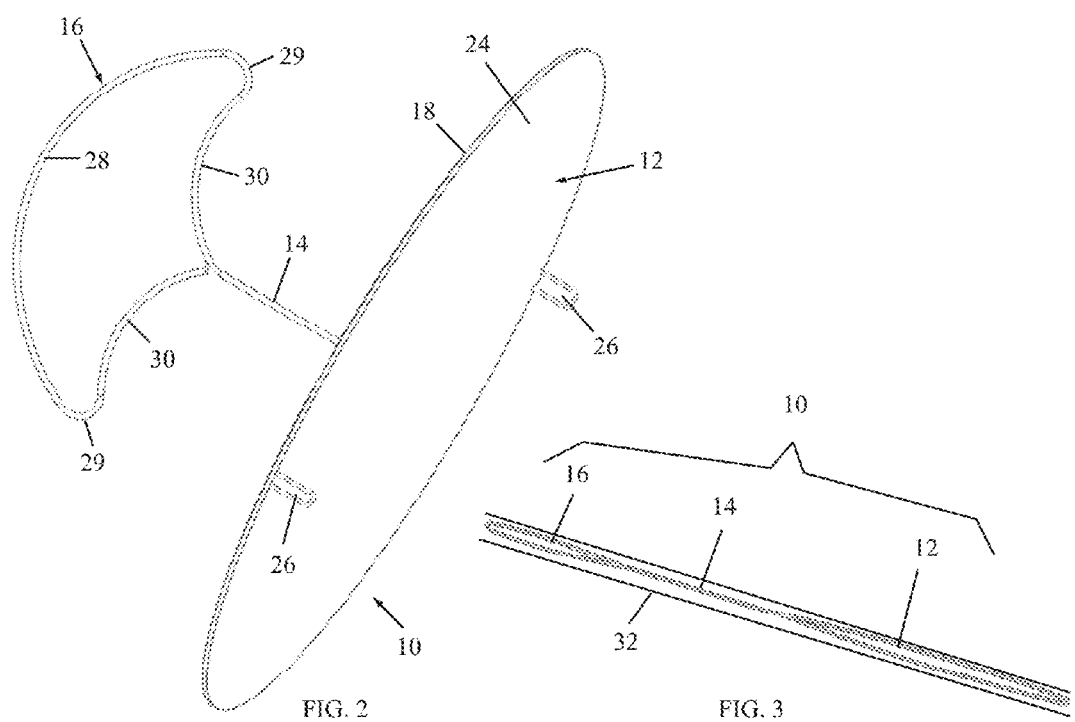
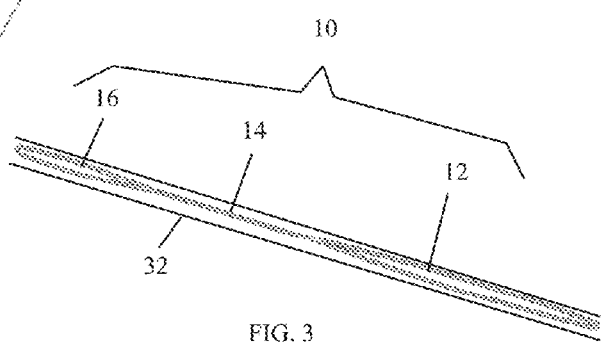
FIG. 1
FIG. 2
FIG. 3

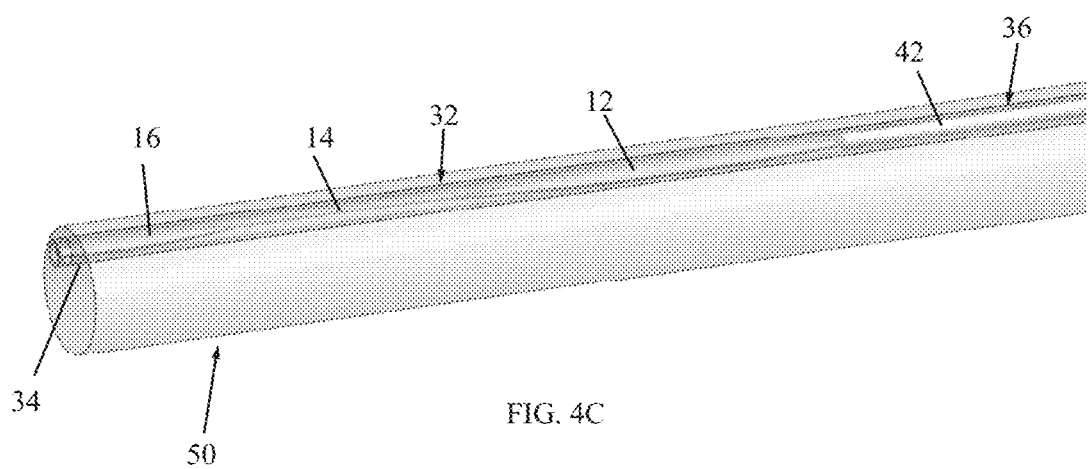

PYLORIC OBSTRUCTION DEVICE

FIELD OF THE INVENTION

The present invention generally relates to devices for obstructing or reducing flow through a body lumen, in particular for obstructing or reducing flow of gastric contents across the pyloric valve.

BACKGROUND OF THE INVENTION

Gastroplasty procedures are known for treating obesity, gastroesophageal reflux disease (GERD), cancer, diabetes and the like. Gastric bypass procedures include the well-known Roux-En-Y procedure, as well as other techniques that reduce the size of the stomach and/or form restrictive barriers, alternative paths, pouches and the like in the stomach or other parts of the gastrointestinal tract. These surgical procedures can be performed with endoscopic tools such as a gastroscope, though traditionally they are performed with open or minimally invasive surgery devices.

In the prior art, when an occlusion of the pylorus is required in the course of a gastroplasty procedure or in a procedure that involves the duodenum, the surgeon staples the pylorus shut (in the stomach) and this is a short term occlusion to allow the duodenum to recover from an operation. Transpyloric devices have also been proposed, which may partially and/or intermittently obstruct the pylorus, thereby decreasing the flow of gastric contents into the duodenum.

PCT Patent Application PCT/US20112/64050 describes a pyloric obstruction device. An obstruction disc is mounted on a proximal portion of a shaft and one or more anchoring members (e.g., rings) are on a distal portion of the shaft. The obstruction disc is delivered to the proximal side of the pylorus and the anchoring members are on the distal side of the pylorus. The rings are sufficiently small to pass through the pylorus.

SUMMARY OF THE INVENTION

The present invention seeks to provide an improved device for obstructing or reducing flow across the pyloric valve (pylorus), as is described more in detail hereinbelow. The device is particularly useful in a transoral gastrointestinal procedure, but the invention is not limited to transoral gastroplasty, and may be used in other laparoscopic, endoscopic, or natural orifice procedures.

The present invention is particularly useful to stop the flow of stomach contents into the proximal gut which includes the duodenum and the initial part of the jejunum. Such a need arises, for example, after creating an alternative path of flow through a gastro-jejunum anastomosis which bypasses the proximal gut. There could be other cases when this need arises, such as after surgery in the duodenum area or in the pancreas or bile outputs to the duodenum. Another indication could be the need to operate endoscopically on the stomach with an inflated stomach. In this case, the plug keeps the inflating air in the stomach and it does not bloat the intestine.

There is thus provided in accordance with an embodiment of the present invention an obstruction device including an obstruction disc mounted on a shaft. The disc includes a membrane attached to a peripheral frame. An anchoring member extends from a distal portion of the shaft. The shaft, anchoring member and peripheral frame together have a unitary construction made from a bent slender element.

BRIEF DESCRIPTION OF THE DRAWINGS

The present invention will be understood and appreciated more fully from the following detailed description taken in conjunction with the drawings in which:

FIGS. 1 and 2 are simplified pictorial illustrations of an obstruction device, constructed and operative in accordance with a non-limiting embodiment of the present invention, in a deployed configuration;

FIG. 3 is a simplified illustration of the obstruction device in a flattened configuration in a delivery tube;

FIG. 4C is a simplified pictorial illustration of the delivery tube and obstruction device mounted in an endoscope.

DETAILED DESCRIPTION OF EMBODIMENTS

Figure 4A:
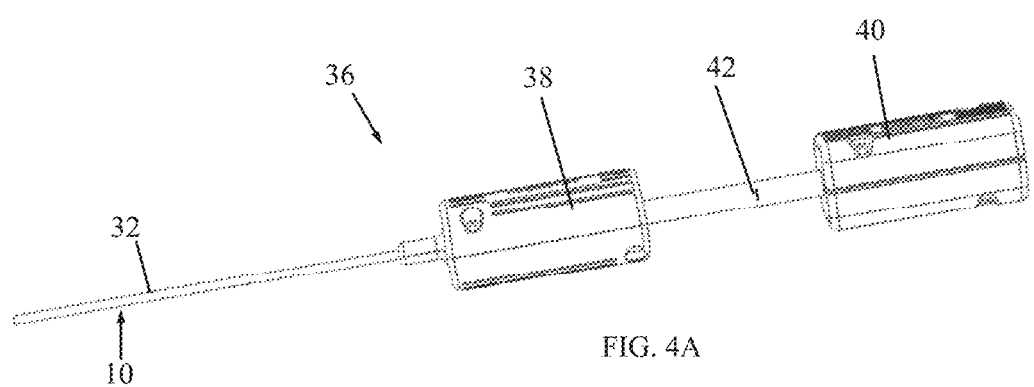
FIG. 4A is a simplified pictorial illustration of the delivery tube and obstruction device mounted in an endoscope tool, in accordance with an embodiment of the present invention.

Reference is now made to FIGS. 1 and 2, which illustrate an obstruction device 10, constructed and operative in accordance with a non-limiting embodiment of the present invention.

Obstruction device 10 includes an obstruction disc 12 mounted on a shaft 14. An anchoring member 16 extends from a distal portion of shaft 14. In a preferred embodiment, obstruction disc 12 includes a peripheral frame 18, which together with shaft 14 and anchoring member 16 have a unitary (one-piece) construction made from a bent wire (or other slender element of any cross-sectional shape), such as from a shape memory alloy (e.g., NITINOL). Alternatively, frame 18, shaft 14 and anchoring member 16 may be made of more than one piece. Shaft 14 may be bent (e.g., generally at 90°) at a central bend point 20 to form an arm 22 (FIG. 1) that extends radially outwards from a central axis (defined as the axis perpendicular to central bend point 20) and which is then curved circumferentially about the central axis to form the peripheral frame 18 of the obstruction disc 12. Arm 22 may be straight or may have a curved shape (as shown in FIG. 1).

Obstruction disc 12 may include a membrane 24, which is attached to peripheral frame 18. Membrane 24 may be sealingly attached to peripheral frame 18 so that the disc is impermeable to air or other fluids, depending on the particular need. Membrane 24 may be made of any medically safe material, such as but not limited to, a plastic, such as silicone, silicone elastomers, latex, polyurethane, PTFE (polytetrafluoroethylene), FEP (fluorinated ethylene propylene), nylon and others. One or more ears 26 may be attached or otherwise extend from the peripheral frame 18 of the obstruction disc 12. For example, ears 26 may be made of a medically safe metal and welded or bonded to the periphery 18. Alternatively, ears 26 may be made or bent from the peripheral frame 18 and as such form a complete one-piece structure with the peripheral frame 18, shaft 14 and anchoring member 16. Ears 26 can be easily grasped by a grasping tool (not shown) for extracting the obstruction device 10, if necessary.

As seen in FIG. 2, the anchoring member 16 may have a crescent shape made of a distal curved portion 28 (which is concave with respect to membrane 24), round corners 29, and round cusps 30 (which are also concave with respect to membrane 24). This shape may be particularly effective in maintaining the device 10 in place and prevent it migrating past the pylorus. The shape is also basically self-centering in the GI tract, which helps align the device properly with the pylorus.

Figure 4B:
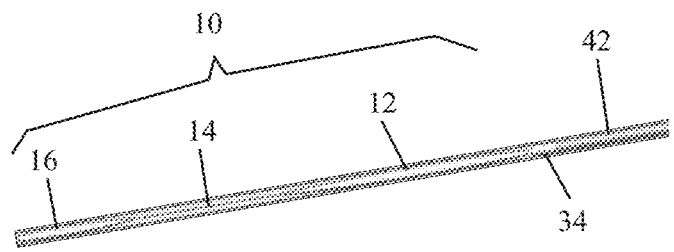
FIG. 4B is a simplified pictorial illustration of the delivery tube and obstruction device mounted in the endoscope tool, showing a pusher used to push the obstruction device out of the delivery tube.

As shown in FIG. 3, in order to deliver the plug (obstruction device) 10, plug 10 is stretched to a flat configuration and placed in a delivery tube 32. As seen in FIG. 4A, delivery tube 32 is assembled with an endoscope tool 36. The tool 36 can be placed in a working channel 34 of an endoscope (e.g., gastroscope) 50 as seen in FIG. 4C. Endoscope tool 36 has a first (e.g., front or distal) handle 38 and a second (e.g., rear or proximal) handle 40. The second handle 40 is operatively connected to a pusher 42 disposed in working channel 34 (FIG. 4B). Pusher 42 is a sliding piston or other suitable element arranged to push against the obstruction disc 12 of obstruction device 10. The first handle 38 is operatively connected to delivery tube 32.

Installation of plug 10 is as follows. The delivery tube 32 with flattened obstruction device 10 is loaded in endoscope tool 36. Endoscope tool 36 is used to deliver delivery tube 32 to the proximal side of the pylorus, and the endoscope tool 36 is moved a little further distally so that the distal end of delivery tube 32 extends into the pylorus. The operator pushes the second handle 40 of the delivery system forward (distally) until the second handle 40 reaches a stop 42 (FIG. 4A). This pushing action causes pusher 42 to push the anchoring member 16 distally out of delivery tube 32, whereupon anchoring member 16 springs out to the deployed configuration of FIGS. 1 and 2. Anchoring member 16 is now deployed distally of the pylorus in the duodenum. The first handle 38 is now pulled rearward (proximally) in order to release the obstruction disc 12 of obstruction device 10 from delivery tube 32, whereupon obstruction disc 12 springs out to the deployed configuration of FIGS. 1 and 2. Obstruction disc 12 is now deployed proximally of the pylorus. Shaft 14 serves as a spacer in the pylorus between obstruction disc 12 and anchoring member 16. The dimensions of shaft 14 are correlated to the usual width of the pylorus muscle. Delivery tube 32 can then be retracted and removed together with the rest of endoscope tool 36. The ears 26 serve for grasping plug 10 for extraction.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An obstruction device comprising:
    an obstruction disc mounted on a shaft, said disc comprising a membrane attached to a peripheral frame; and
    an anchoring member extending from a distal portion of said shaft, wherein said shaft is bent at a central bend point to form an arm that extends radially outwards from a central axis and which is then curved circumferentially about the central axis to form said peripheral frame, and wherein said anchoring member has a crescent shape made of a distal curved portion, round corners, and round cusps.

2. The obstruction device according to claim 1, wherein said membrane is sealingly attached to said peripheral frame.

3. The obstruction device according to claim 1, wherein said bent slender element is made of a shape memory alloy.

4. The obstruction device according to claim 1, wherein said arm is curved.

5. The obstruction device according to claim 1, wherein one or more ears extend from said peripheral frame.

6. The obstruction device according to claim 1, further comprising a delivery tube in which said obstruction device is disposed in a flattened configuration.

7. The obstruction device according to claim 6, further comprising an endoscope having a working channel in which said delivery tube and said obstruction device are mounted.

8. The obstruction device according to claim 7, comprising a pusher operative to push said delivery tube distally out of said working channel.

* * * * *